United States Patent [19]

Kurihara et al.

[11] Patent Number: 4,999,139

[45] Date of Patent: Mar. 12, 1991

[54] ORGANIC NONLINEAR OPTICAL MATERIAL AND NONLINEAR OPTICAL DEVICE

[75] Inventors: Takashi Kurihara, Mito; Shiro Matsumoto, Iruma; Toshikuni Kainou, Mito; Hirohisa Kanbara, Yokohama; Kenichi Kubodera, Isehara, all of Japan

[73] Assignee: Nippon Telegraph and Telephone Corporation, Tokyo, Japan

[21] Appl. No.: 481,460

[22] Filed: Feb. 16, 1990

[30] Foreign Application Priority Data

Jan. 27, 1988 [JP] Japan .................................. 63-14394
Jan. 24, 1989 [JP] Japan .................................. 1-14379

[51] Int. Cl.$^5$ .......................... F21V 9/04; G02B 5/22; G02B 6/10
[52] U.S. Cl. ..................................... 252/587; 252/582; 350/1.1; 350/3.64; 350/96.12; 350/96.3; 350/354
[58] Field of Search ............... 252/582, 587; 350/1.1, 350/354, 3.64, 96.12, 96.3

[56] References Cited

U.S. PATENT DOCUMENTS

| | | | |
|---|---|---|---|
| 4,428,873 | 1/1984 | Murayama et al. | 252/583 |
| 4,692,636 | 9/1987 | Wang | 252/587 X |
| 4,720,355 | 1/1988 | De Martino | 252/582 |
| 4,859,876 | 8/1989 | Dirk et al. | 252/582 X |

FOREIGN PATENT DOCUMENTS 61-167930 7/1986 Japan .
112414 1/1982 Poland .................. 252/587

OTHER PUBLICATIONS

Williams, D. J., Angew Chem. Int. Ed. Engl. 23, 690, 1984.
Li, D. et al., Chem. Phys. Lett. 131 (4,5) 370, 1986.
Cowan, D. O. et al., AFOSR Report A185402, 1986.
Chemical Abstracts, vol. 87, No. 21, Nov. 21, 1977, p. 502, col. 1, abstract No. 167114y, Columbus, Ohio, U.S.; V. Samarenko et al., "Mechanism of the addition of Sodium Bisulfite to an Activated Double Bond", & Zh. Org. Khim, 1977, vol. 13(8), pp. 1790–1791.
Optics Letters, vol. 13, No. 1, Jan. 1988, pp. 24–26, Tsububa, Ibaraki, JP; M. Yamashita et al.: "Intracavity Femtosecond-Pulse Compression with the Addition of Highly Nonlinear Organic Materials"* p. 24*.
Chemical Abstracts, vol. 103, No. 11, Sep. 16, 1985, p. 583, col. 2, abstract No. 87 598t, Columbus, Ohio, U.S.; J. Bielawski et al.: "Some New Beta–Nitrostyrene Fungicides." & Tagungsbericht der Akad. Landwirtschaftswiss. DDR, 1984, No. 222, pp. 283–292.

(List continued on next page.)

*Primary Examiner*—John S. Maples
*Assistant Examiner*—Richard Treanor
*Attorney, Agent, or Firm*—Frishauf, Holtz, Goodman & Woodward

[57] ABSTRACT

A nonlinear optical device having an optical medium and an optical element including a polarizer, an optical resonator and a reflector is provided. The optical medium includes an organic nonlinear optical material represented by a formula:

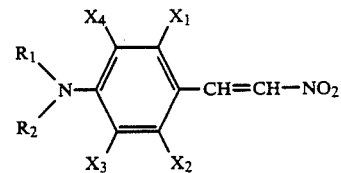

wherein each of $R_1$ and $R_2$ is an alkyl group having 2 to 6 carbon atoms or a hydroxyalkyl group having 2 to 6 carbon atoms, $R_1$ and $R_2$ being same or different groups; or $R_1$ is an ethyl group and $R_2$ is an acryloyloxyethyl group ($CH_2$=$CH$—$COO$—$CH_2CH_2$—) or a methacryloyloxyethyl group ($CH_2$=$C(CH_3)$—$COO$—$CH_2C$-$H_2$—); and each of $X_1$, $X_2$, $X_3$, and $X_4$ is individually a hydrogen atom, a hydroxyl group, a halogen atom, an alkyl group, an alkoxy group, an alkyl ester group, or an alkylamide group, where $X_1$, $X_2$, $X_3$ and $X_4$ may be the same or different groups.

13 Claims, 4 Drawing Sheets

OTHER PUBLICATIONS

J. L. Oudar, Optical Nonlinearities of Conjugated Molecules. Stilbene Derivatives and Highly Polar Aromatic Compounds, J. Chem. Physics, vol. 67, No. 2, Jul. 1977, pp. 446–457.

G. I. Stegemen et al., Third-Order Nonlinear Guided-Wave Optics, Proceeding of SPIE, The International Society for Optical Engineering, vol. 682, pp. 179–186 (1986).

E. P. Ippen et al., Appl. Phys. Lett. 26 (3), p. 92 (1975).

Organic Materials for Second Harmonic Generation, Tweig, R. J., IBM Report 1985, UCRL—15706.

Vizgert, R. V. et al., Sou. J. Quint. Electron 12, 214, 1982.

Bielawski, J. et al., CA 103(11): 87598t.

ORGANIC NONLINEAR OPTICAL MATERIAL AND NONLINEAR OPTICAL DEVICE

This is a division of application Ser. No. 07/302,579 filed Jan. 26, 1989 now abandoned.

BACKGROUND OF THE INVENTION

1. Field of Art

The present invention relates to organic nonlinear optical materials and nonlinear optical devices in which nonlinear refractive indices of the organic nonlinear optical materials are utilized.

2. Prior Art

Third-order nonlinear optical materials attract attention as important materials for optical devices in the future because they exhibit frequency conversion functions due to third harmonic generations (hereinafter referred to as THG) and additionally they are applicable for optical switching and optical memory while making use of their optical bistable behavior. Particularly, organic nonlinear optical materials have the following advantages superior over the known inorganic materials. Initially, when compared with crystalline inorganic ferroelectrics such as KDP (potassium dihydrogenphosphate), $KH_2PO_4$ and $LiNbO_3$ (lithium niobate), the organic nonlinear optical materials have larger nonlinear optical coefficients showing the second order nonlinear characteristics. Secondly, when compared with an inorganic semiconductor such as gallium arsenide (Ga-As), the organic nonlinear optical materials have ultrafast response times. Thirdly, different from copper(I) chloride (CuCl) exhibiting a fast response and being capable of operating at room temperature, but being hardly fabricated in a thin film with a thickness of micrometer order, the organic nonlinear optical materials can be easily fabricated into thin films with the thickness of micrometer order. The organic nonlinear optical materials have the possibility of satisfying all requirements which have not been satisfied by the known materials, and thus eager investigations of such materials are continued. For example, the following references disclose organic nonlinear optical materials.

J. L. Oudar, J. Chem. Phys., Vol 67, No. 2, pp 446 to 457 (1977), "Optical Nonlinearities of Conjugated Molecules. Stilbene Derivatives and Highly Polar Aromatic Compounds." This reference discloses the results of studies on the second- and third-order hyperpolarizabilities $\beta$ and $\alpha$ of 4-dimethylamino-$\beta$-nitrostyrene in addition to the derivatives of stilbene. Another reference is G. I. Stegeman and C. T. Seaton, Proceedings of SPIE—The International Society for Optical Engineering, 682, pp 179 to 186 (1986), "Third-order Nonlinear Guided-Wave Optics."

The known third-order nonlinear optical materials include the following two groups of materials. The first group includes $\pi$-conjugated polymers, the typical being polydiacetylene, particularly 2,4-hexadiyne-1,6-bis(p-toluenesulfonate) and polyacetylene. The second group includes low molecular weight compounds each having substituents disposed asymmetrically to serve as a donor and an acceptor, the typical being aminonitrostilbene, particularly 4-(N,N-diethylamino)-4'-nitrostilbene. In these compounds, the dimethylamino and diethylamino groups serve as the donors and nitro and cyano groups serve as the acceptors.

The optical nonlinearies of the $\pi$-conjugated polymers are based on the polarization of free electrons in the valence electron band, and thus the $\pi$-conjugated polymers have the disadvantage resembling that of inorganic semiconductor materials in that the response time is delayed by the resonance effect due to a narrow band gap. Moreover, a $\pi$-conjugated polymer that is superior over PTS (2,4-hexadiyne-1,6-bis(p-toluenesulfonate)) has not yet been found.

Since the low molecular weight compounds having asymmetrically disposed substituents serving as a donor and an acceptor exhibit nonlinear optical effects superior over that of 4-(N,N-diethylamino)-4'-nitrostilbene, it have been tried to introduce a longer $\pi$-conjugated chain in the compound and to introduce a more active donor-acceptor pair in the compound. However, torsion of the $\pi$-conjugated chain is induced as the length of the $\pi$-conjugated chain in the compound is increased, leading to the result that the effective length of the $\pi$-conjugated chain (i.e. the effective length of delocalized electrons) is decreased. On the other hand, when a more active donor-acceptor pair is introduced in a compound, spontaneous polarization is enhanced leading to the result that the difference in dipole moment between the ground state and the excitation state cannot be increased so large as expected. In addition, deterioration of the material due to absorption of light and delay in response time is accerelated. As the molecular size becomes larger and the spontaneous polarization of the nonlinear optical material becomes extremely enhanced, the solubility in a solvent or a high polymer matrix is lowered and crystallization property is deteriorated to have poor processibility for the preparation of an optical element therefrom.

However, the compounds having substituents disposed asymmetrically and serving as a donor and an acceptor are important organic materials for eager investigations since they exhibit high speed and highly efficient nonlinear optical responses although they have the aforementioned complicated problems.

OBJECTS AND SUMMARY OF THE INVENTION

The object of this invention is to provide an organic nonlinear optical material which exhibits a high speed and highly efficient nonlinear optical response and which is improved in solubility not only for organic solvents, but also polymeric materials with excellent transparency and crystallization property to form a large size crystal.

A nonlinear optical device utilizing an organic material has been known, in which an input power ($P_i$) is a gating pulse light to obtain an output power light responsive to the wave form of the gate pulses. In this connection, reference should be made to E. P. Ippen and C. V. Shank, Appl. Phys. Lett., 26 (3), 92 (1975).

Figure 1:
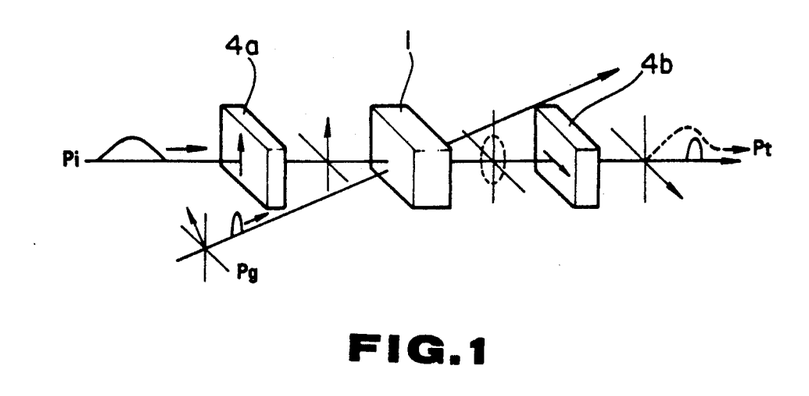
FIG. 1 is a view showing diagrammatically the construction of a known nonlinear optical device and an optical switch.

FIG. 1 shows diagrammatically a known nonlinear optical device.

Referring to FIG. 1, polarizers 4a and 4b are disposed with their polarization axes perpendicular with each other. A nonlinear refractive index kerr medium 1 comprises a 1 mm thick glass cell containing liquid carbon disulfide ($CS_2$). With the construction shown in FIG. 1, the linear polarization of the input power transmitting through the polarizer 4a is converted to the elliptical polarization due to the change in refractive index of the nonlinear refractive index kerr medium 1 as far as gate pulses $P_g$ are supplied. As the result, a portion of the input light can transmit through the perpendicular polarizer 4b, and thus the input power is optically switched by the gate light pulses.

The relative signal intensity T of the input power takes the maximum intensity when the angle between the polarized gate light and the input power is 45°. The relative signal intensity T is represented by the following equations (1) and (2).

$$T = \sin^2(\Delta\phi/2) \quad (1)$$

$$\Delta\phi = 2\pi n_2 L I_{in}/\lambda \quad (2)$$

In the equations set forth above, L is the length of the nonlinear refractive index kerr medium, $\lambda$ is the wavelength of the input power, $I_{in}$ is the intensity of the gate light, $n_2$ is the nonlinear refractive index. When is sufficiently small, the equation (1) may be transformed as follows.

$$T \alpha n_2^2 L^2 I_{in}^2 \quad (3)$$

It will be seen from equation (3) that T is in proportion to the square of $n_2$. This known $CS_2$ optically-gated optical switch was prepared and tested. When $\lambda$ was 0.83 $\mu$m, L was 1 mm and $I_{in}$ was 300 MW/cm², the relative signal intensity T was 1%. Substituting these results into the equations (1) and (2), the nonlinear refractive index $n_2$ was calculated as follows.

$$n_2 = 8.8 \times 10^{-14} \text{ cm}^2/\text{W} \quad (4)$$

The nonlinear susceptivity $\chi^{(3)}$ was calculated from the value of $n_2$ to find that $\chi^{(3)} = 4.2 \times 10^{-12}$ e.s.u.

The known $CS_2$ type optically-gated optical switch exhibits a high speed response time in the order of 1 picosecond and thus can be used for instantaneous photographing or in a high speed spectrographic measuring apparatus. However, the nonlinear refractive index of the known $CS_2$ optically-gated optical switch is not so high, and thus it requires that the gate light has an extremely high intensity.

Accordingly, another object of this invention is to provide a high speed and highly efficient nonlinear optical device which is operative with a light having a relatively low light intensity.

A principal feature of the organic nonlinear optical material, according to this invention, resides in that it has a remarkably high nonlinear response efficiency as a nonlinear optical material made of a low molecular weight compound in which substituents serving as a donor and an acceptor are asymmetrically disposed in the molecule. Secondly, the material of this invention is improved in processibility in that it can be dissolved in a variety of solvents and polymer matrices to form concentrated solutions or in that a large single crystal can be formed therefrom.

The organic nonlinear optical materials provided by this invention are derivatives of $\beta$-nitrostyrene having a substituted amino group at the para position as represented by the following general formula (1) or derivatives of p-($\beta$-nitroethylenyl)-julolidine another type of conjugated system stylene represented by the following general formula (2).

wherein each of $R_1$ and $R_2$ of the substituted amino group at the para position stands for an alkyl or hydroxyalkyl group having 2 to 6 carbon atoms, $R_1$ and $R_2$ being same or different groups; and $X_1$, $X_2$, $X_3$ and $X_4$ each stands for at least one selected from the group consisting of hydrogen atom, hydroxyl group, halogen atoms, alkyl groups, alkoxy groups, alkyl ester groups and alkylamide groups, $X_1$, $X_2$, $X_3$ and $X_4$ being the same or different groups.

wherein $X_1$ and $X_2$ may be the same or different groups and each stands for hydrogen atom, hydroxyl group, a halogen atom, an alkyl group, an alkoxy group, an alkyl ester group or an alkylamide group.

The present invention further provides a nonlinear optical device comprising an optical medium and an optical element including a polarizer, an optical resonator and a reflector, said optical medium comprising an organic nonlinear optical material selected from the group consisting of derivatives (1) of 4-(N,N-dialkyl)amino-$\beta$-nitrostyrene and derivatives (2) of p-($\beta$-nitroethylenyl)-julolidine.

DESCRIPTION OF PREFERRED EMBODIMENTS

It is an important feature of the organic nonlinear optical material of this invention that the structure having the π-conjugated chain is styrene or julolidine. The styrene or julolidine structure has a higher nonlinear polarizability per a unit volume than the stilbene structure which has a larger number of π-electrons. Furthermore, since the styrene structure or julolidine structure is compact, the organic nonlinear optical materials of this invention having the styrene structures or julolidine structures are superior over the compounds having stilbene or other structures in solubility in solvents and polymer matrices and also improved in crystallization property to form larger size crystals.

In the derivatives of 4-(N,N-dialkyl)amino-β-nitrostyrene constituting the organic nonlinear optical materials of this invention, the behavior as an electron donator and the solubility of the material are effectively improved when both of $R_1$ and $R_2$ are ethyl groups or $R_1$ is an ethyl group and $R_2$ is a hydroxyl ethyl group.

The structure having the electron donating positions as represented by the general formula (2) attributes the delocalization of π-electrons by the strong conjugation of π-electrons in the ring and the lone electron pair of the amine group and the improvement in solubility due to the bulkness of the methylene group.

All of $X_1$, $X_2$, $X_3$ and $X_4$ attached to the benzene ring of 4-(N,N-diethyl)amino-β-nitrostyrene and $X_1$ and $X_2$ of p-(β-nitroethylenyl)-julolidine may be hydrogen to exhibit an enhanced effect, and likewise an enhanced effect may be obtained when either one of these substituents is a hydroxyl group, a halogen atom, an alkyl group, an alkoxy group, an alkyl ester group or an alkylamide group with the remaining substituents being hydrogen.

All of the derivatives of 4-(N,N-diethyl)amino-β-nitrostyrene, according to this invention, are excellent in solubility and thus polymer matrices may be doped therewith in high concentration. The derivatives of 4-(N,N-diethyl)-amino-β-nitrostyrene, according to this invention, may be dissolved in a variety of organic solvents to give concentrated solutions. Particularly, they may be dissolved in organic solvents each having a dielectric constant higher than that of chloroform, and may also be dissolved in a mixture of organic solvents each having a dielectric constant higher than that of chloroform with other organic solvents to give concentrated solutions. Particularly preferred solvents are those each having an aromatic ring and having a dielectric constant higher than that of chloroform. For example, poly(methyl methacrylate) may be doped with 4-(N,N-diethyl)amino-β-nitrostyrene by a process comprising the steps of dissolving 4-(N,N-diethyl)amino-β-nitrostyrene in acetone, dissolving poly(methyl methacrylate) in acetone, mixing the solution of 4-(N,N-diethyl)amino-β-nitrostyrene in acetone together with the solution of poly(methyl methacrylate) in acetone, and then removing acetone from the mixed solution.

Alternatively, a transparent polymer may be doped with an organic nonlinear optical material of this invention by the steps of melting the transparent polymer to fluidize the same, adding the organic nonlinear optial material of this invention to the molten transparent polymer, mixing and then cooling to solidify the transparent polymer. Transparent polymers which may be used as the matrix materials for the organic nonliner optical materials of this invention include polymers, copolymers and mixtures thereof.

The known p-(N,N-dimethyl)amino-β-nitrostyrene is poor in solubility in organic solvents. For example, the solubility thereof is only 5 wt % in dimethylformamide and only 2 wt % in ethanol. In contrast thereto, the solubility of 4-(N,N-diethyl)amino-β-nitrostyrene provided by this invention is more than 50 wt % in dimethylformamide and more than 40 wt % in ethanol. Likewise, the solubility of p-(N-ethyl-N-hydroxyethylamino)-β-nitrostyrene in a variety of organic solvents is more than 30 wt %.

Only 2.5 wt % of diethylamino-β-nitrostilbene can be dissolved in poly(methyl methacrylate) at the most. In contrast thereto, 30 wt % or more of 4-(N,N-diethyl)amino-β-nitrostyrene can be dissolved in poly(methyl methacrylate). Likewise, 25 wt % or more of p-(N-ethyl-N-hydroxyethylamino)-β-nitrostyrene can be dissolved in poly(methyl methacrylate).

It is difficult to form a large size single crystal of the known N,N-dimethylamino-β-nitrostyrene by recrystallization from a solution thereof in a solvent, the maximum dimensions of the obtainable single crystal being 3 mm×5 mm×10 mm. A larger single crystal of a derivative of p-(N,N-diethyl)amino-β-nitrostyrene may be easily obtained by recrystallization from a solution thereof in a solvent, the dimensions of the obtainable single crystal being 8 mm×10 mm×50 mm or more.

In the derivatives of 4-(N,N-dialkyl)amino-β-nitrostyrene constituting the organic nonlinear optical materials of this invention, when either one of $R_1$ and $R_2$ is an hydroxyalkyl group and the other is an alkyl group, the hydroxyl group of the hydroxyalkyl group may be reacted with acrylic acid, methacrylic acid or alkyl esters of acrylic or methacrylic acid to introduce an acryloxy or methacryloxy group in the resultant compound. For example, when acrylic acid is reacted with a derivative of amino-β-nitrostyrene having a hydroxyethyl group, a derivative of amino-β-nitrostyrene having an acryloyloxy group bonded to an ethyl group is produced as represented by the following reaction equation of:

$CH_2=CHCOOH\ +$

A polymer-form nonlinear optical material having the dye attached structure may be obtained by polymerizing 4-(N-acryloyloxyethyl-N-ethyl)amino-β-nitrostyrene with methyl methacrylate in the presence of a polymerization catalyst.

Likewise, by using methacrylic acid or esters of methacrylic acid, 4-(N-methacryloyloxyethyl-N-ethyl-)amino-β-nitrostyrene may be prepared, and they may be copolymerized with various monomers forming transparent polymers to obtain nonlinear optical polymers having dye attached structures.

In the derivatives of 4-(N,N-dialkyl)amino-β-nitrostyrene used as the organic nonlinear optical materials of this invention and having substituents $X_1$, $X_2$, $X_3$ and $X_4$ wherein at least one of them is a hydroxyl group, acryloyl or methacryloyl group may be introduced by reacting the hydroxyl group attached to the benzene ring with a variety of derivatives of acrylic or methacrylic acid.

The thus prepared 4-(N,N-dialkyl)amino-β-nitro-2-acryloyloxystyrene may be copolymerized with a monomer which forms a transparent polymer in the presence of a polymerization catalyst to prepare a nonlinear optical polymer having a dye attached structure. Likewise, by using a derivative of methacrylic acid, a methacryloyloxy group may be introduced into the benzene ring.

When either one of $X_1$ or $X_2$ of p-(β-nitroethylenyl)-julolidine used as the organic nonlinear optical material is substituted by a hydroxyl group, the substituting hydroxyl group may be converted to an acryloyloxy or a methacryloyloxy group by reacting the substituting hydroxyl group with a derivative of acrylic or methacrylic acid. Thus, a polymer usable as the nonlinear optical material and having a dye attached structure, as represented by the following structural formula, may be prepared by copolymerization with a monomer forming a transparent polymer.

In the structural formule set forth above, $\underline{m}$ and $\underline{n}$ stand for molar fractions of the compolymerized monomers.

Typical examples of the organic nonlinear optical materials according to this invention will be set forth hereinbelow.

4-(N,N-diethyl)amino-β-nitrostyrene; DEANST 4-(β-nitroethylenyl)julolidine; JANST 4-(N-ethyl-N-hydroxyethyl)amino-β-nitrostyrene; EO-EANST 4-(N,N-diethyl)amino-β-nitro-2-hydroxystyrene; Oh-DEANST 4-(N,N-diethyl)amino-β-nitrostyrene poly(methyl methacrylate) (doping); DEANST-PMMA 4-(N,N-diethyl)amino-β-nitrostyrene-Poly(2,2,3,3-tetrafluoropropyl Methacrylate-Methylmethacrylate Copolymer; DEANST-Fluoro resin-MMA Copolymer 4-(N-ethyl-N-acryloyloxyethyl)amino-β-nitrostyrene-Methyl Methacrylate Copolymer; (DEANST-AP)-MMA Copolymer 4-(N,N-diethyl)amino-β-nitro-2-chlorostyrene; Cl-DEANST 4-(N,N-diethyl)amino-β-nitro-3-methoxystyrene; MeO-DEANST 4-(N,N-diethyl)amino-β-nitro-3-acetoxystyrene; AcO-DEANST 4-(N,N-diethyl)amino-β-nitro-2-methylstyrene; Me-DEANST 4-(N,N-diethyl)amino-β-nitro-2-acetylaminostyrene; AcNH-DEANST The organic nonlinear optical materials, according to this invention, exhibit enhanced third-order nonlinear optical properties. They are also improved in crystallization property and solubility, and thus large crystals with excellent characteristics and polymer films can be easily fabricated from them. The organic nonlinear optical materials of this invention may be dissolved in solvents having high dielectric constants, such as nitrobenzene, and the solutions are contained in sealed optical cells to prepare optical media each having a high nonlinear refractive index. It had not been known until we found that the nonlinear refractive index was variable by differing the used solvent. It is preferable to use a solvent which has a dielectric constant higher than that of chroloform. Examples of preferable solvents include N-methylacetoamide, N-methylformamide, formamide, acetoamide, dimethylformamide, N,N-dimethylacetoamide, acetonitrile, nitromethane, acrylonitrile, methanol, diethylene glycol, benzonitrile, ethanol, acetoaldehyde, propanol, benzaldehyde, benzil alcohol and pyridine.

A nonlinear refractive kerr medium may be fabricated by dissolving 4-(N,N-diethyl)amino-$\beta$-nitrostyrene according to this invention in a transparent polymer material followed by solidification of the polymer material.

Alternatively, a transparent polymer is melted and an organic nonlinear optical material of this invention is added thereto, followed by mixing and cooling to solidify the mixture, whereby an optical medium is produced. As a still further process for the preparation of a nonlinear refractive kerr medium, a single crystal of 4-(N,N-diethyl)amino-$\beta$-nitrostyrene is prepared since a large single crystal can be formed from the material of this invention.

The thus prepared nonlinear refractive kerr medium may be used as an essential element for a low optical power operative optically gated optical switch, a bistable device for optical instruments and a phase-conjugated-wave-generator, and also used for the production of an optical integrated element for optical communication systems.

EXAMPLES OF THE INVENTION

The present invention will now be described in more detail with reference to some examples thereof taken in conjunction with the appended drawings.

EXAMPLE 1

Synthesis of 4-(N,N-diethyl)amino-$\beta$-nitrostyrene (DEANST)

A solution was prepared by dissolving 118 grams (0.57 mol) of p-(N,N-diethyl)aminobenzaldehyde in 500 ml of nitromethane, and added with 17 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from ethanol for two times. An amount of 107 grams of red crystals was obtained. The yield was 75%.

Figure 2:
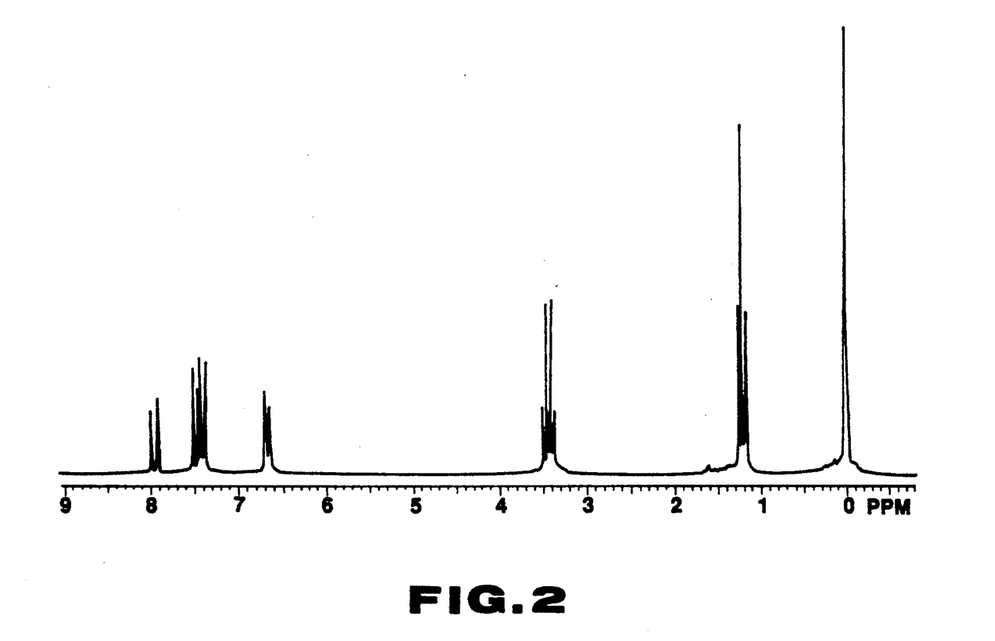
FIG. 2 is a chart showing the ¹HNMR of 4-(N,N-diethyl)amino-$\beta$-nitrostyrene of this invention.

The product, p-(N,N-diethyl)amino-$\beta$-nitrostyrene, had a melting point of 95° C. The $^1$H-NMR spectrum of the product is shown in FIG. 2, and details of the NMR analysis are set forth below.

Solvent: CDCl$_3$, $\delta_{C\text{-}H}$ (aromatic and vinyl): 6.8 to 8.0 ppm, $\delta_{C\text{-}H}$ (methyl): 1.2 ppm, $\delta_{C\text{-}H}$ (methylene): 3.4 ppm.

Elemental Analysis: $C_{12}H_{16}N_2O_2$ (MW=220.27), Cald.: C 65.44, H 7.32, N 12.72, Found: C 65.57, H 7.20, N 12.92.

EXAMPLE 2

Synthesis of p-($\beta$-nitroethylenyl)-julolidine (JANST)

A solution was prepared by dissolving 60 grams (0.3 mol) of p-formyljulolidine in 250 ml of nitromethane, and added with 8 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from methanol for two times. An amount of 50 grams of red crystals was obtained. The yield was 69%.

EXAMPLE 3

Synthesis of 4-(N-ethyl-N-hydroxyethyl)amino-$\beta$-nitrostyrene (EOEANST)

A solution was prepared by dissolving 60 grams (0.31 mol) of 4-(N-ethyl-N-hydroxyethyl)aminobenzaldehyde in 250 ml of nitromethane, and added with 8 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 42 grams of red crystals was obtained. The yield was 66%.

EXAMPLE 4

Synthesis of 4-(N,N-diethyl)amino-$\beta$-nitro-2-hydroxystyrene (Oh-DEANST)

A solution was prepared by dissolving 60 grams (0.31 mol) of 2-hydroxy-4-(N,N-diethyl)aminobenzaldehyde in 250 ml of nitromethane, and added with 8 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 34 grams of red crystals was obtained. The yield was 53%.

EXAMPLE 5

Synthesis of 4-(N,N-diethyl)amino-$\beta$-nitro-3-chlorostyrene

A solution was prepared by dissolving 34 grams (0.16 mol) of 3-chloro-4-(N,N-diethyl)aminobenzaldehyde in 150 ml of nitromethane, and added with 5 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 16 grams of red crystals was obtained. The yield was 39%.

EXAMPLE 6

Synthesis of 4-(N,N-diethyl)amino-β-nitro-2-methoxystyrene (MeO-DEANST)

A solution was prepared by dissolving 30 grams (0.14 mol) of 2-methoxy-4-(N,N-diethylamino)benzaldehyde in 150 ml of nitromethane, and added with 4 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 16 grams of red crystals was obtained. The yield was 44%.

EXAMPLE 7

Synthesis of 4-(N,N-diethyl)amino-β-nitro-2-acetyloxystyrene (AcO-DEANST)

A solution was prepared by dissolving 23.5 grams (0.10 mol) of 2-acetyloxy-4-(N,N-diethylamino)benzaldehyde in 100 ml of nitromethane, and added with 3 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 10 grams of red crystals was obtained. The yield was 36%.

EXAMPLE 8

Synthesis of 4-(N,N-diethyl)amino-β-nitro-3-methylstyrene (Me-DEANST)

A solution was prepared by dissolving 30 grams (0.16 mol) of 3-methyl-4-(N,N-diethylamino)benzaldehyde in 150 ml of nitromethane, and added with 5 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 17 grams of red crystals was obtained. The yield was 45%.

EXAMPLE 9

Synthesis of 4-(N,N-diethyl)amino-β-nitro-3-acetylaminostyrene (AcNH-DEANST)

A solution was prepared by dissolving 28 grams (0.12 mol) of 3-acetylamino-4-(N,N-diethylamino)benzaldehyde in 120 ml of nitromethane, and added with 4 grams of ammonium acetate. The mixture was heated at 100° C. for 5 hours under agitation. The reaction solution was then cooled on a dry ice-acetone bath until crystallization had been completed. The separated solid (crystal) was filtered off and dried in vacuum. The obtained product was recrystallized from acetonitrile for two times. An amount of 10 grams of red crystals was obtained. The yield was 36%.

EXAMPLE 10

Preparation of 4-(N,N-diethyl)amino-β-nitrostyrene(DEANST)-/Polymethylmethacrylate(PMMA) (Doping)

Figure 3:
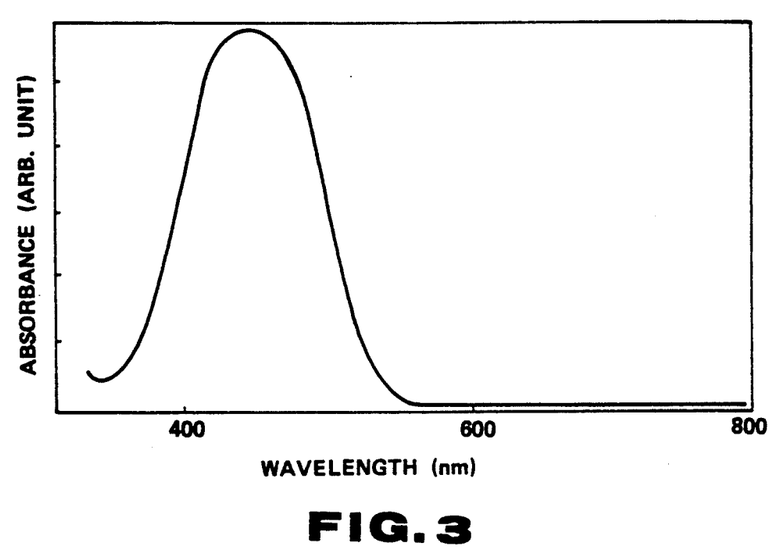
FIG. 3 is a chart showing the visible light absorption spectrum of a thin PMMA film doped with 4-(N,N-diethyl)amino-$\beta$-nitrostyrene according to this invention.

A 9.8 wt % solution of p-(N,N-diethyl)amino-β-nitrostyrene in chloroform and a 18.2 wt % solution of poly(methyl methacrylate) in chloroform were mixed in a mixing ratio of 1:1. The mixed solution was coated on a glass plate by spin coating to form a 1 micron thick film of 35 wt % p-(N,N-diethyl)amino-β-nitrostyrene-polymethyl methacrylate. The visible light absorption spectrum of the thus produced film is shown in FIG. 3.

EXAMPLE 11

Preparation of 4-(N,N-diethyl)amino-β-nitrostyrene(-DEANST)/(2,2,3,3-tetrafluoropropylmethacrylate(-Fluoro Resin)-MMA Copolymer A 12 wt % solution of 4-(N,N-diethyl)amino-β-nitrostyrene in acetone and a 18 wt % solution of a 2:1 copolymer of 2,2,3,3-tetrafluoropropylmethacrylate/-methyl methacrylate in acetone in a mixing ratio of 1:1. The mixed solution was coated on a glass plate by spin coating to form a 1.5 micron thick film of 40 wt % 4-(N,N-diethyl)amino-β-nitrostyrene(-DEANST)/2,2,3,3-tetrafluoropropylmethacrylate-MMA copolymer.

EXAMPLE 12

Synthesis of 4-(N-ethyl-N-acryloyloxyethyl)amino-β-nitrostyrene(-DEANST-Ap)/Methyl Methacrylate(MMA) Copolymer A solution was prepared by dissolving 4.5 grams of methyl methacrylate, 24.2 grams of 4-(N-ethyl-N-(2-acryloyloxyethyl)amino)-β-nitrostyrene and 0.14 gram of 2,2'-azobis(2-methylpropanenitrile) in 70 ml of dehydrated dioxane. The solution was charged in a glass polymerization ample, followed by evacuation and sealing, and then the solution was allowed to react at 60° C. for 24 hours. The reaction solution was poured into hexane, whereby a precipitate was separated. The precipitate was filtered and then rinsed with methanol. The rinsed precipitate was dried to obtain a product polymer. The molar fraction of the copolymer was 0.3 for MMA and 0.7 for DEANST-Ap. The following is the structural formula of the copolymer.

EXAMPLE 13

A neodymium-yttrium-aluminium garnet (Nd-YAG) laser was used as the light source for the measurement of the third harmonic generation (THG). The laser had a wavelength of 1.06 μm and an intensity of 50 MW/cm$^2$. After filtering visible light, the laser beam was focused by a lens and irradiated on a sample and the light rays emitted from the sample was passed through a filter so that only the intensity of THG was detected while using an photo-multiplier tube. The sample subjected to measurement was prepared by pulverizing a crystal of an organic nonlinear material to adjust the particle size to 105 to 120 microns. In order to ascertain that the origin of the THG was not the second-order cascading in third-order nonlinear optical processes, as observed in urea or 2-methyl-4-nitroaniline (MNA), but the pure THG effect, the second harmonic generation (hereinafter referred to as SHG) of the same sample was measured. Table 1 shows the results of measurements of harmonic generation intensities for the organic nonlinear optical materials of this invention and for comparative samples.

The relative SHG intensities compared to urea of individual samples are shown in the third column of Table 1, which reveal that the results are approximately zero ($\approx 0$). This means that the measured results are not the second-order cascading in third-order nonlinear processes (w+2w→3w), but show pure third-order effects. In the fourth column of the Table, the relative THG intensities compared to p-nitroaniline are shown. As shown, the organic nonlinear optical materials of this invention have the relative THG intensities ranging from 300 to 720, whereas the results of the comparative samples or comparative examples range from 50 to 80. The compounds used in the Comparative Examples will be set forth below.

1. 4-(N,N-dimethylamino)-β-nitrostyre, DMA-NS
2. 4-(N,N-diethylamino)-4'-nitrostilbene, DEANS
3. 4-(β-nitrophenonyl)ethylennyl-julolidine, JANS
4. 4-(N,N-dimethyl)amino-β-nitro-2-hydroxystyrene, Oh-DMANST

TABLE 1

| Example No. | Organic Nonlinear Optical Material | Relative intensity of SHG to Urea Ratio | Relative Intensity of THG to p-Nitroaniline Ratio |
|---|---|---|---|
| Working Examples of the Invention | | | |
| 1 | DEANST | ≈0 | 720 |
| 2 | JANST | ≈0 | 500 |
| 3 | EOEANST | ≈0 | 680 |
| 4 | Oh-DEANST. | ≈0 | 630 |
| 5 | Cl-DEANST | ≈0 | 480 |
| 6 | MeO-Deanst | ≈0 | 460 |
| 7 | AcO-DEANST | ≈0 | 560 |
| 8 | Me-DEANST | ≈0 | 510 |
| 9 | Ac-NH-DEANST | ≈0 | 450 |
| 10 | DEANST-PMMA (Doping) | ≈0 | 300 |
| 11 | DEANST-Fluoro Resin/MMA Copolymer | ≈0 | 320 |
| 12 | DEANST-Ap-MMA Copolymer | ≈0 | 400 |
| Comparative Examples (Comparative Samples) | | | |
| 1 | DMA-NS | ≈0 | 50 |
| 2 | DEANS | ≈0 | 60 |
| 3 | JANS | ≈0 | 80 |
| 4 | Oh-DMANST | ≈0 | 60 |

EXAMPLE 14

An optically-gated optical switch device, in which p-(N,N-diethyl)amino-β-nitrostyrene prepared by Example 1 is used as an optical medium, will now be described.

A solution prepared by dissolving p-(N,N-diethyl)-amino-β-nitrostyrene in dimethylformamide (DMF, ε=37.8) was contained in a sealed glass vessel to be used as a nonlinear refractive index kerr medium. The other parts of the construction of the device were the same as shown in FIG. 2.

Figure 4:
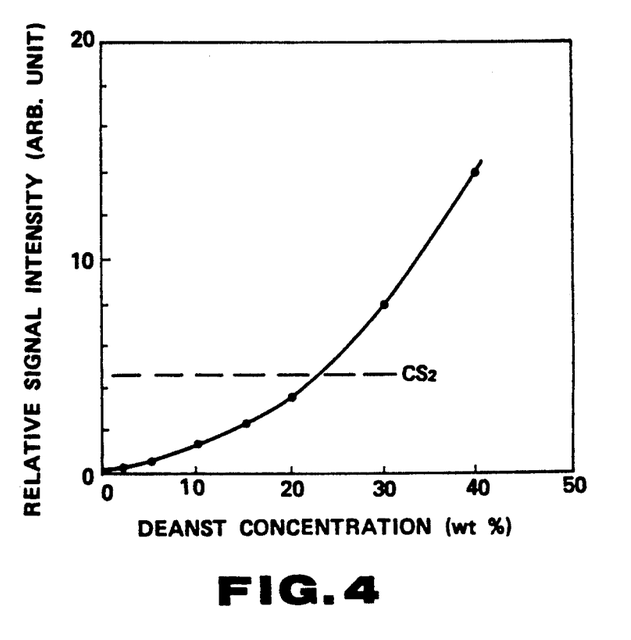
FIG. 4 is a graph showing the relative signal intensity in terms of the concentration (wt %) of 4-(N,N-diethyl)amino-$\beta$-nitrostyrene dissolved in dimethylformamide.

FIG. 4 shows the change in relative signal intensity of the optical switch in terms of the change in concentration of 4-(N,N-diethyl)amino-β-nitrostyrene. As seen from FIG. 4, the instantaneous transmittance is increased in proportion to the second power of the intensity. As the concentration is increased above 23 wt %, the instantaneous transmittance exceeds the instantaneous transmittance of liquid carbon disulfide (CS$_2$) which has been well known and used widely to date. The nonlinear refractive index n$_2$ of the medium when the concentration of 4-(N,N-diethyl)amino-β-nitrostyrene is 40 wt % was calculated from Equation (3) set forth hereinbefore to find that n$_2$ took the following value.

$$n_2 = 1.5 \times 10^{-13} \, cm^2/W (\chi^{(3)} = 7.3 \times 10^{-12} \, e.s.u.)$$

Figure 5:
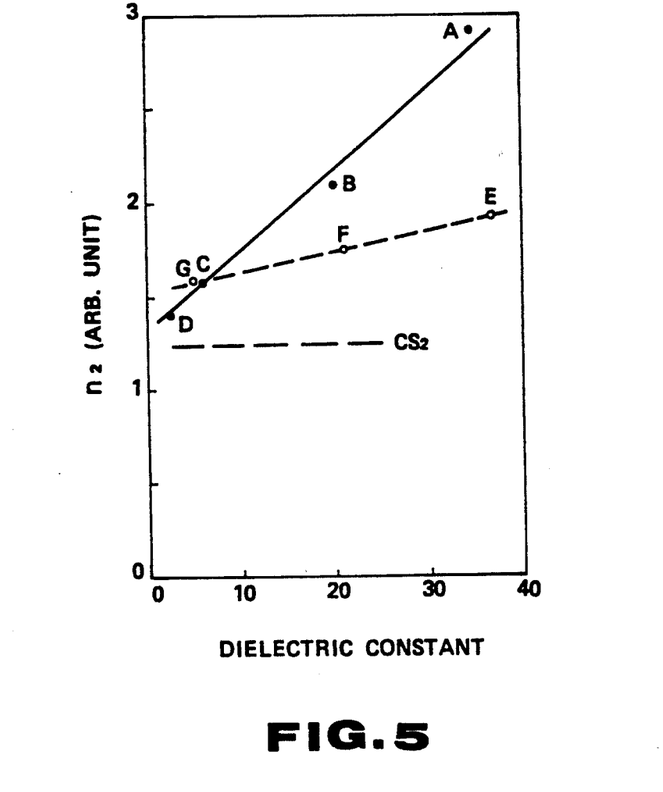
FIG. 5 shows the change in nonlinear refractive index $n_2$ of 4-(N,N-diethyl)amino-$\beta$-nitrostyrene dissolved in various solvents.

The abscissa of the graph of FIG. 5 indicates the dielectric constant of various solvents used for dissolving the organic nonlinear optical material of the invention, individual solvents being used at the same molar concentration. The nonlinear refractive indices n$_2$ of the organic nonlinear optical materials when dissolved in individual solvents are plotted in the graph in terms of the dielectric constants of respective solvent group. The used solvents are aromatic solvents including nitrobenzene (A), a mixture of nitrobenzene and chlorobenzene (B), chlorobenzene (C) and benzene (D), and non-aromatic system solvents including dimethylformamide (E), acetone (F) and chloroform (G).

As seen from FIG. 5, the value of n$_2$ becomes larger as the dielectric constant of the used solvent is higher, and aromatic solvent groups are generally more preferable than non-aromatic system solvents. The highest efficiency was obtained when 4-(N,N-diethyl)amino-β-nitrostyrene was dissolved in nitrobenzene in an amount corresponding to the highest dissoluble concentration. At that time, n$_2$ took the value of $2.2 \times 10^{-13}$ cm$^2$/W. The value was about 2.5 times as high as that obtainable by using the known CS$_2$. The found effect indicated by the transmittance was about six times (2.5$^2$=6.25) as high as that obtainable by the use of CS$_2$. Search and identification of optimal solvents disclosed herein are the pioneer work done by us.

EXAMPLE 15

Figure 6:
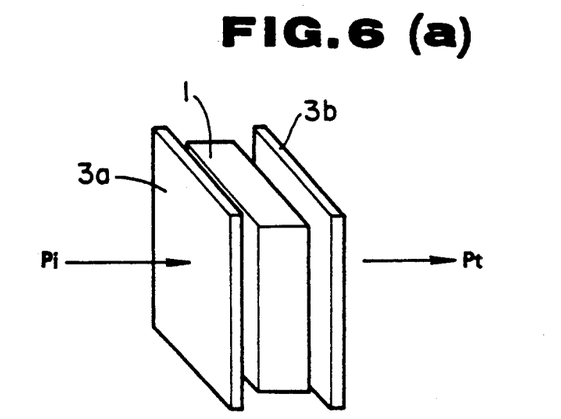
FIG. 6(a) is a schematic illustration of a nonlinear optical device according to this invention.
FIG. 6(b) is a chart showing the limitter operation of the device shown in FIG. 6(a)
FIG. 6(c) is a chart showing the bistable operation of the device shown in FIG. 6(a)

Another embodiment of the nonlinear optical device according to this invention, is shown in FIG. 6(a). A nonlinear optical kerr medium 1 comprises a solution of 4-(N,N-diethyl)amino-β-nitrostyrene dissolved in a solvent, and the medium is disposed between to mirrors 3a and 3b each of which is made of a multi-layered film of ferroelectic material reflecting 90% of input light and transmitting the remaining 10% of input light. The medium 1 and the opposing mirrors 3a and 3b constitute an optical resonator.

The aforementioned device may be operated by varying the wavelength of input light a little or by changing the resonator length, i.e. the spacing between the mirrors 3a and 3b, so that the resonator is adjusted to resonate.

In this device, a light ray having a wavelength of 1.064 microns from an Nd-YAG laser was used, and the device was actuated by changing the resonator length. The interrelations between the intensity of input power $P_i$ and the intensity of output power $P_t$ are shown in FIGS. 6(b) and 6(c) to find that the limiting operation and the bistable operation took place. In each of FIGS. 6(b) and 6(c), the abscissa indicates the input power $P_i$ and the ordinate indicates the output power (signal) $P_t$.

The minimum input power ($P_i^{min}$) can be analytically obtained from the following equation of:

$$P_i^{min} = (K\lambda)/(n_2 l);$$

wherein $\lambda$ is the wavelength of used light, l is the length of the optical medium, k is a coefficient determined by the reflectivity of a mirror and the adjustment of resonator length and generally taking a value of about 0.001. When the effective output of the pulse oscillation is set to 50 mW and a semiconductor laser having an oscillation wavelength of 0.83 micrometer is used, the intensity of output power is calculated to be $6 \times 10^6$ W/cm$^2$ by focusing the beam diameter to 1 micrometer. The intensity of the output power is sufficiently high as compared to the minimum input power $P_i^{min}$ of the aforementioned nonlinear optical device at that wavelength. This nonlinear optical device, according to this invention, could be operated while using a semiconductor laser as the light source.

The response time of 4-(N,N-diethyl)amino-$\beta$-nitrostyrene of this invention is estimated to be approximately $10^{-12}$ second. However, the response time of the device is determined by the longer one of the response time of the used medium and the lifetime $t_p$ of a photon in the oscillator. The lifetime of a photon $t_p$ is calculated from the following equation of:

$$t_p = -1_{op}/(c \times \ln R);$$

wherein $1_{op}$ is the wavelength of the oscillator, c is the velocity of light, and R is the reflectivity of the mirror.

The lifetime of a photon is calculated to be $6 \times 10^{-11}$ seconds and thus $t_p > t$ so that the lifetime of a photon determines the response time of the device. It is thus ascertained that the response time of this embodiment of the invention is shorter than $10^{-10}$ second.

EXAMPLE 16

Figure 7:
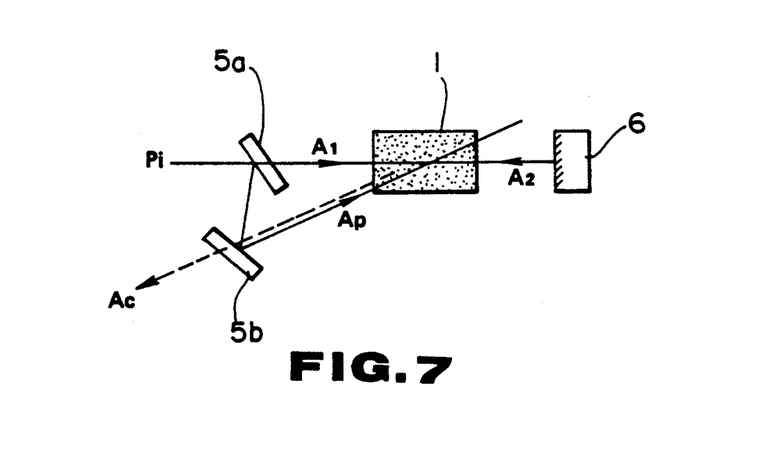
FIG. 7 is a schematic illustration of a phase conjugated wave generator according to this invention.

A phase conjugated wave generator according to this invention will now be described with reference to FIG. 7. The device comprises half-mirrors 5a, 5ba, reflector 6 and a liquid optical medium 1 composed of 4-(N,N-diethyl)amino-$\beta$-nitrostyrene described in Example 14. The device is an optical alignment referred to as a degenerated four wave mixing. In detail, when three input light waves, i.e., a light wave $A_1$, a light wave $A_2$ incident from the direction reverse to the incident direction of the light wave $A_1$ and a light wave $A_p$ incident obliquely, are incident upon an optical medium having a nonlinear optical refractive index, the fourth light wave $A_c$ where conjugated in regard to the light wave $A_p$ only the special phase term is generated. The phase-conjugated-wave attracts attention in the image processing technology as it may be effectively used for correction of an image or an effective means for real time holography.

It was ascertained that the device of this embodiment exhibited a high speed response could be operated with an input power of relatively low intensity.

What is claimed is:

1. A nonlinear optical device comprising an optical medium and an optical element including a polarizer, an optical resonator and a reflector, said optical medium comprising an organic nonlinear optical material represented by the formula:

wherein each of $R_1$ and $R_2$ is an alkyl group having 2 to 6 carbon atoms or a hydroxyalkyl group having 2 to 6 carbon atoms, $R_1$ and $R_2$ being same or different groups; or $R_1$ is an ethyl group and $R_2$ is a group selected from the group consisting of an acryloyloxyethyl group and a methacryloyloxyethyl group; and each of $X_1$, $X_2$, $X_3$, and $X_4$ is individually a hydrogen atom, a hydroxyl group, a halogen atom, an alkyl group, an alkoxy group, an alkyl ester group, or an alkylamide group, where $X_1$, $X_2$, $X_3$ and $X_4$ are the same or different groups.

2. The nonlinear optical device according to claim 1, wherein said organic nonlinear optical material is dissolved in an organic solvent having a dielectric constant higher than that of chloroform, or dissolved in a mixed solvent of an organic solvent having a dielectric constant higher than that of chloroform with one or more other organic solvents.

3. The nonlinear optical device according to claim 2, wherein said organic solvent has a dielectric constant higher than that of chloroform and has an aromatic ring, and wherein said mixed solvent is a mixture of an organic solvent having a dielectric constant higher than that of chloroform and having an aromatic ring with one or more other organic solvents.

4. The nonlinear optical device according to claim 1, wherein said optical medium comprises said organic nonlinear optical material dissolved in a transparent polymer material followed by solidification.

5. The nonlinear optical device according to claim 4, wherein said transparent polymer material is selected from the group consisting of polymers each having a refractive index substantially equal to or less than that of poly(methyl methacrylate), copolymers each having a refractive index substantially equal to or less than that of poly(methyl methacrylate), and mixtures thereof.

6. The nonlinear optical device according to claim 1, wherein said optical medium comprises a crystalline medium which is formed by crystallization of said organic nonlinear optical material.

7. The nonlinear optical device according to claim 2, wherein the solvent is selected from the group consisting of N-methylacetoamide, N-methylformamide, formamide, acetoamide, dimethylformamide, N,N-dimethylacetoamide, acetonitrile, nitromethane, acrylonitrile, methanol, diethylene glycol, benzonitrile, ethanol, acetoaldehyde, propanol, benzaldehyde, benzil alcohol and pyridine.

8. The nonlinear optical device according to claim 1, wherein the nonlinear optical material is 4-(N-N-diethyl)amino-$\beta$-nirostyrene.

9. The nonlinear optical device according to claim 1, wherein the nonlinear optical material is selected from the group consisting of 4-(N-ethyl-N-hydroxyethyl)amino-$\beta$-nitrostyrene, 4-(N,N-diethyl)amino-$\beta$-nitro-2-hydroxystyrene, 4-(N-ethyl-N-acryloyloxyethyl)amino-$\beta$-nitrostyrene, 4-(N,N-diethyl)amino-$\beta$-nitro-3-methoxystyrene, 4-(N,N-diethyl)amino-$\beta$-nitro-2-methylstyrene and 4-(N-ethyl-N-methacryloyloxyethyl)amino-$\beta$-nitrostyrene.

10. The nonlinear optical device according to claim 2, wherein the solvent is selected from the group consisting of nitrobenzene, chlorobenzene, benzene, acetone and a mixture of nitrobenzene and chlorobenzene.

11. The nonlinear optical device according to claim 2, wherein the reflector is a pair of mirrors.

12. The nonlinear optical device according to claim 11, wherein the mirrors are made of a multi-layered film of ferroelectric material.

13. The nonlinear optical device according to claim 12, wherein the medium is 4-(N,N-diethyl)amino-$\beta$-nitrostyrene dissolved in a solvent.

* * * * *

UNITED STATES PATENT AND TRADEMARK OFFICE
CERTIFICATE OF CORRECTION

PATENT NO. : 4,999,139

DATED : March 12, 1991

INVENTOR(S) : KURIHARA et al

It is certified that error appears in the above-identified patent and that said Letters Patent is hereby corrected as shown below:

Title page:

Section [75] Inventors: Change "Toshikuni Kainou" to

--Toshikuni Kaino--.

Left column, insert the following:

--[63] Related U.S. Application Data

Division of Ser. No.302,579 filed Jan. 26, 1989--.

Signed and Sealed this

Sixth Day of October, 1992

*Attest:*

DOUGLAS B. COMER

*Attesting Officer*    *Acting Commissioner of Patents and Trademarks*